United States Patent [19]

Janes et al.

[11] Patent Number: 5,280,788
[45] Date of Patent: Jan. 25, 1994

[54] DEVICES AND METHODS FOR OPTICAL DIAGNOSIS OF TISSUE

[75] Inventors: G. Sargent Janes, Lincoln; Gary B. Hayes, Leominster, both of Mass.

[73] Assignee: Massachusetts Institute of Technology, Cambridge, Mass.

[21] Appl. No.: 661,072

[22] Filed: Feb. 26, 1991

[51] Int. Cl.⁵ .............................................. A61B 5/00
[52] U.S. Cl. .................................. 128/665; 128/6
[58] Field of Search ................. 128/634, 665-667, 128/6; 606/9, 15-16

[56] References Cited

U.S. PATENT DOCUMENTS

| | | |
|---|---|---|
| 3,467,098 | 9/1969 | Ayres . |
| 3,693,623 | 9/1972 | Harte et al. . |
| 3,821,510 | 6/1974 | Muncheryan . |
| 3,961,621 | 6/1976 | Northeved . |
| 4,126,136 | 11/1978 | Auth et al. . |
| 4,213,462 | 7/1980 | Sato . |
| 4,269,192 | 5/1981 | Matsuo .............................. 128/665 |
| 4,311,138 | 2/1982 | Sugarman . |
| 4,336,809 | 6/1982 | Clark . |
| 4,449,535 | 5/1984 | Renault ............................ 128/634 |
| 4,524,770 | 6/1985 | Orandi . |
| 4,564,011 | 1/1986 | Goldman . |
| 4,566,438 | 1/1986 | Liese et al. ........................ 606/16 |
| 4,567,882 | 2/1986 | Heller . |
| 4,598,715 | 7/1986 | Mächler et al. .................. 128/634 |
| 4,622,974 | 11/1986 | Coleman et al. . |
| 4,623,789 | 11/1986 | Ikeda et al. ...................... 128/634 X |
| 4,627,435 | 12/1986 | Hoskin ............................. 606/16 X |
| 4,693,244 | 9/1987 | Daikuzono ........................ 606/16 |
| 4,752,115 | 6/1988 | Murray, Jr. et al. ............. 128/665 X |
| 4,834,093 | 5/1989 | Littleford ......................... 606/15 X |
| 4,967,745 | 11/1990 | Hayes et al. . |
| 5,032,123 | 7/1991 | Katz et al. ....................... 606/15 |
| 5,078,711 | 1/1992 | Kakami et al. ................... 606/16 |

FOREIGN PATENT DOCUMENTS

PCT/EP89/-
00385 10/1989 PCT Int'l Appl. .
PCT/US90/-
01498 10/1990 PCT Int'l Appl. .

*Primary Examiner*—Francis Jaworski
*Attorney, Agent, or Firm*—Hamilton, Brook, Smith & Reynolds

[57] ABSTRACT

The present invention relates to systems and methods employed in the use of spectroscopy in the diagnosis of tissue. More particularly, it relates to the use of surface contact and needle probe devices having one or more optical fibers used to direct laser radiation onto tissue to be diagnosed, collecting radiation subsequently emitted by the tissue and delivering that radiation to a system for spectral analysis.

50 Claims, 11 Drawing Sheets

DEVICES AND METHODS FOR OPTICAL DIAGNOSIS OF TISSUE

RELATED U.S. APPLICATION

"Systems and Methods of Molecular Spectroscopy to Provide for the Diagnosis of Tissue" filed on Feb. 26, 1991 by Richard P. Rava, Joseph J. Baraga, and Michael S. Feld corresponding to U.S. Ser. No. 661,077.

BACKGROUND OF THE INVENTION

The present invention relates generally to the field of optical systems employed in the diagnosis and treatment of tissue, and, more particularly, to the use of contact devices in the spectroscopic characterization of tissue.

Traditional methods of diagnosing tissue within the human body have employed invasive and time consuming techniques such as biopsy procedures to provide accurate diagnosis, and non-invasive techniques such as radiological or magnetic resonance imaging to provide less detailed but useful information as to the condition of tissue. Biopsies involve the removal of tissue from the region of interest where the sample can be subjected to detailed diagnostic, histologic or biochemical study to determine the nature and extent of disease.

An alternative to tissue biopsy is the use of spectroscopy as a diagnostic tool. This type of procedure has been developed in conjunction with the use of stains or dyes which provide or enhance spectroscopic features associated with certain types or stages of disease.

However the in vivo applications of these techniques are limited due to the difficulties and the expense in delivering the diagnostic marker to the site or region of interest and due to the limited understanding of the spectral information produced.

When tissue is irradiated, a number of mechanisms occur including fluorescence, elastic and inelastic scattering, absorption and reflection of light. These mechanisms produce complicated spectra from which the diagnostically useful information can be extracted. These spectra, when compared with the spectra of normal tissue, can indicate the nature and extent of diseases.

SUMMARY OF THE INVENTION

The optical fiber laser needle of the present invention is a contact device which provides controlled two way light transmission to and from a point or region of tissue to be diagnosed. This device provides specific diagnostic information at selected points within a region of tissue or tissues being examined in real time. The device employs light having selected characteristics such that when tissue is illuminated it emits light that contains diagnostically useful information about the tissue. Applications encompass the diagnosis of many organs including those traditionally viewed using endoscopic techniques. The present invention finds particular application in the diagnosis of cancerous or pre-cancerous lesions but can be used generally to detect the presence and concentration of particular molecular constituents of tissue at any desired site. This information can be employed to diagnose the precise condition of tissue.

The present optical needle and its diagnostic system provide a substantial improvement in the speed of diagnosis over current biopsy techniques. Furthermore, there are electronic data display techniques which can be employed to augment its utility as a fast survey device. The device employs the various mechanisms by which light is directed onto and reemitted or absorbed by tissue to produce diagnostically significant information.

One embodiment of the optical fiber laser needle of the present invention is a single pixel device with the distinguishing characteristic of making local point measurements of tissue at points beneath the surface with minimum trauma. Using a single fiber to deliver light to the tissue to be diagnosed, this device utilizes the same spectroscopic data bases which contain the information used to perform comparative diagnostic analysis of tissue surface. This embodiment can be used with an endoscope whereby the needle can be inserted at selected locations within the body and used in conjunction with other endoscopic procedures. Alternatively, a multifiber-optical needle device can be employed to provide more detailed information regarding the tissue being examined.

The optical fiber laser needle complements the spectroscopic imaging and surface contact systems referenced above. The optical needle uses essentially the same electronics and laser systems with only minimal changes in the external operating system. The optical needle has many applications serving, for example, as a stand alone tool for breast, brain, and liver biopsies permitting biopsies to be taken along a penetration path as opposed to a singular surface point. The optical needle can be guided by ultrasound, x-rays, or steriostatic positioning devices. It can also use the spectroscopic data itself to evaluate the type of tissue present at each point along the path of penetration, something which is not easily done with x-rays or other non-invasive methods.

A preferred embodiment involves incorporating the needle in a "bayonet" biopsy tool which acts as a guide in deciding when to take tissue samples. Finally, in addition to its utility as a diagnostic device, the optical needle is suited for site specific therapeutic treatment because of its ability to concentrate and deliver laser flux, at high energy levels relative to diagnostic applications, to specific remote locations without complex lens systems.

A preferred embodiment of the optical needle employs an optically transparent material having a converging channel terminating at a cutting edge. The needle tip is generally cylindrical with a tapered distal surface that forms the converging channel. The converging channel provides for the focussing of light that is being directed onto the tissue which is in contact with the tapered distal surface of the needle adjacent to the cutting edge. The cutting edge is constructed to minimize trauma to the tissue into which the device is being inserted.

The converging channel formed by the tapered surface reduces the cross-sectional area of the device such that light proceeding along the channel towards the tip becomes progressively more divergent as it is internally reflected by the surface of the needle. As the angle of incidence of the light against the tapered surface exceeds a critical angle, it is refracted through the wall of the needle and into the tissue. This convergent geometry also acts as an efficient wide angle collector of the resultant fluorescence light which is channeled into one or more optical fibers to the spectral analyzer.

One or more optical fibers can be employed to deliver light radiation to the convergent channel and to collect light emitted by the tissue. The collected light is then directed to a spectroscopic analyzer which compares selected characteristics of the collected light with a data base of information. This data base contains the information necessary for the particular type of tissue and the diseased or abnormal conditions thereof sought to be diagnosed. Thus the analyzer compares the light emitted by the tissue with a reference signal to provide the diagnostic information of interest. This reference signal can be a single spectrum of adjacent healthy tissue, or can be drawn from a standardized database constructed from empirical information, or from a model of tissue response.

Various types of light are emitted by the tissue in response to illumination at different wavelengths or bands of radiation. The illuminating radiation selected can be dependent upon the depth of penetration into the tissue to be diagnosed. For some applications, diagnostic information is needed for only a few microns adjacent to the contact surface of the device. Ultraviolet or visible light would then be appropriate to perform diagnostic measurements. Alternatively, it is desirable in certain applications to obtain diagnostic information deeper within tissue without further needle or probe penetration. In this embodiment, infrared wavelengths can be employed to produce Raman shifts in the light emitted by the tissue which are collected by the needle or probe for analysis.

One preferred embodiment employs a bundle of fibers coupled to single optically conductive needle tip. Another preferred embodiment employs the fiber bundle itself with the distal tip formed into a needle configuration and inserted into a hypodermic needle. Another preferred embodiment employs a channel or groove extending through the distal tip which cuts and isolates a thin tissue section for optical diagnosis into the tissue to be diagnosed.

The above features and other aspects of the invention, either as combinations and parts of the invention or as steps of the method will now be more particularly described with reference to the accompanying drawings and pointed out in the claims. It will be understood that the embodiments of the invention are shown by way of illustration only and not as limitations of the invention. The principal features of this invention can be employed in various embodiments without departing from the scope of the invention.

DETAILED DESCRIPTION OF THE INVENTION

In the development of tissue spectroscopy employed for diagnosis and treatment, it is imperative to provide a controlled optical interface contacting the tissue to reduce or eliminate situations in which variations in the relative contribution of fluorescence, scattering, and absorption produce uncertainties in the interpretation of the data. The optical needle of the present invention provides this controlled interface using a convergent optical channel. The delivery, retrieval and analysis of light directed through this convergent channel is described in connection with FIG. 1.

Figure 1:
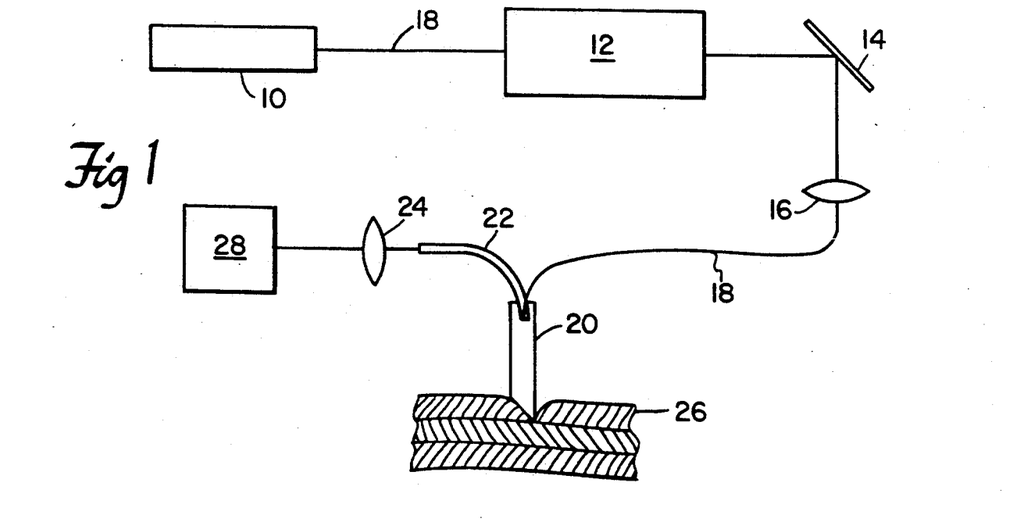
FIG. 1 is a schematic illustration of a preferred embodiment of the diagnostic system of the present invention.

FIG. 1 illustrates in schematic form one embodiment of the optical system that can be employed in the diagnostic system of the present invention. A laser 10 or other suitable light source provides light of a selected wavelength or band of wavelengths through an optical fiber or fiber bundle 18 to a spectral filtering device 12. The filtering device 12 is used to precisely select the desired wavelength or band of wavelengths for the procedure. The light is reflected from a mirror 14 and through lens 16 or any other suitable optical circuit to direct the desired light output to the needle or probe 20 that contacts the tissue 26 under study. The light enters the tissue 26 causing it to absorb and emit light through various mechanisms including fluorescence and scattering. In one method the upper layer 26 is analyzed, the needle 20 is then further displaced into tissue to analyze the underlying layers to provide a diagnostic profile as a function of depth.

A distal end of optical fiber 22 is positioned in proximity to the distal surface of fiber 18 that is used to irradiate the tissue 26 through needle 20. The distal end of fiber 22, receives the radiation emitted by the tissue and directs the light through lens 24 and into spectrometer 28 or other systems suitable for analysis of the radiation emitted by the tissue. Spectrometer 28 can be replaced with a number of narrow band filters and detectors to collect the spectral data. Any number of commercially available spectral analyzer systems can be employed.

The present invention takes advantage of the flux concentration properties of converging transparent needle or optical fiber tips in order to provide reproducible, efficient and controlled two-way light transmission into and out of subsurface tissue.

The general properties of this type of optical system include the well known optical "Brightness Theorem" which defines the manner in which light behaves when directed into a converging channel. When light is directed into or out of a converging optical channel with smooth, perfectly reflecting walls, the product of beam area and beam divergence is conserved. If the walls converge to a tip of zero cross section, the beam will ultimately be directed back onto itself.

If the reflectance mechanism at the walls of such a converging channel is total internal reflection, then the angle of incidence which increases with each succeeding reflection will ultimately permit the light to escape when its angle of incidence exceeds a "critical angle". Note that light which escapes by exceeding the "critical angle" will be preferentially directed in the forward direction. Where the walls at the tip are specular but not metallized (e.g., dielectric), this light transmission process will be reversible and the tip of the channel will act as an efficient flux collector and beam collimator for light which impinges on it from the outside. Note that in one embodiment, the walls at the tip of the device are not specular thereby providing for better recovery of light emitted by the tissue.

Figure 2A:
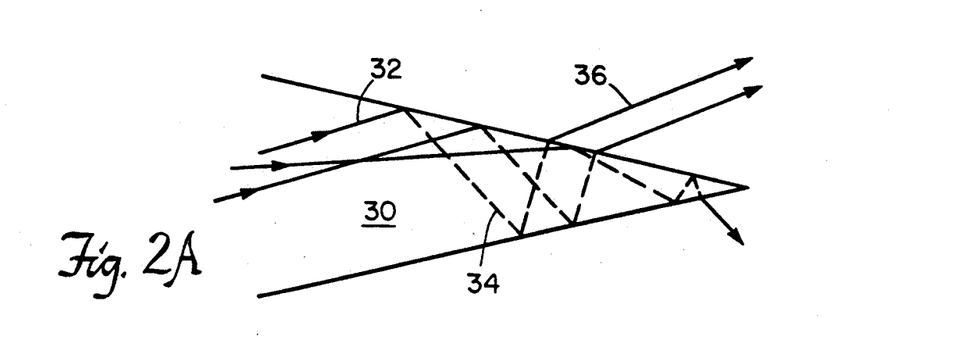
FIG. 2A is a schematic illustration of the increasing divergence of a light beam as it progresses along a converging optical channel.
Figure 2B:
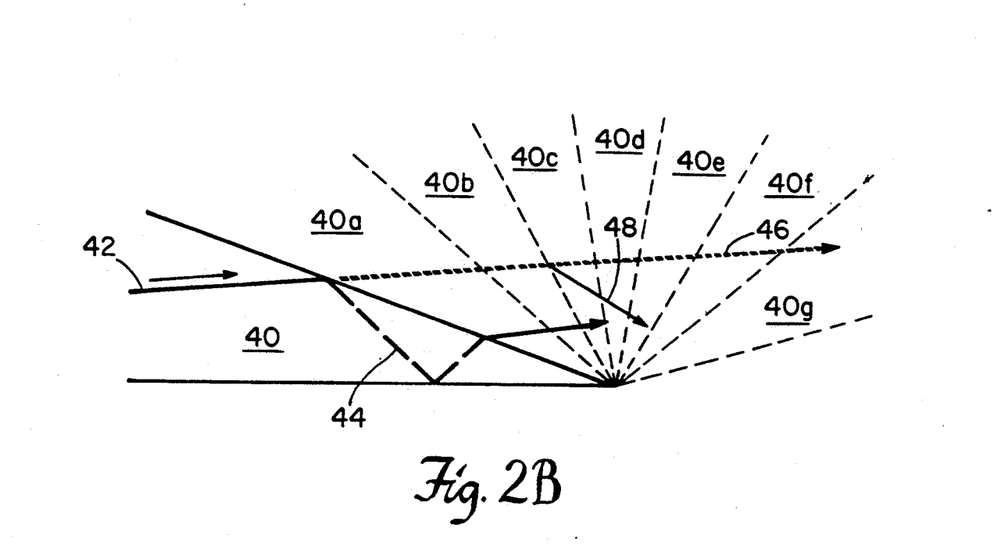
FIG. 2B is a schematic illustration of the application of the method of "Phantom Cones" to understand the operation of an optical needle.

These phenomena are illustrated in FIGS. 2A and 2B. FIG. 2A is a schematic diagram illustrating the increasing divergence of a light beam as it enters a converging optical channel. FIG. 2B illustrates the method of "phantom cones" which can be used to visualize and calculate the details of this process in two dimensional systems. By reflecting the cone to form imaginary cones 40a-40g, instead of the light beam, the beam can be represented as a straight line 46 leading to easy visualization of the turn around and escape conditions. Note that the ray 48 shown in FIG. 2B leaves the cone on the third dielectric bounce. If the surfaces had instead been simple metallic mirrors, the ray would not have left the cone. It would instead have started to bounce back after the fourth bounce in cone 40d, and exited out of cone 40g after the eighth bounce.

This process of internal reflection and transmission is presented more fully in any available discussion of the Fresnelequation. There remains some probability of reflection when the angle exceeds the critical angle. However, this probability decreases with the following encounter with the cone surface.

Note that large ray angles following escape from the dielectric tend to be forbidden because most of the photons escape preferentially in a direction more closely parallel to the exterior surface once the interior angle of incidence exceeds the critical angle. A number of device configurations stem from the concepts illustrated by the foregoing analysis including those of FIGS. 3-5 which illustrate three embodiments of the optical needle device.

Figure 3A:
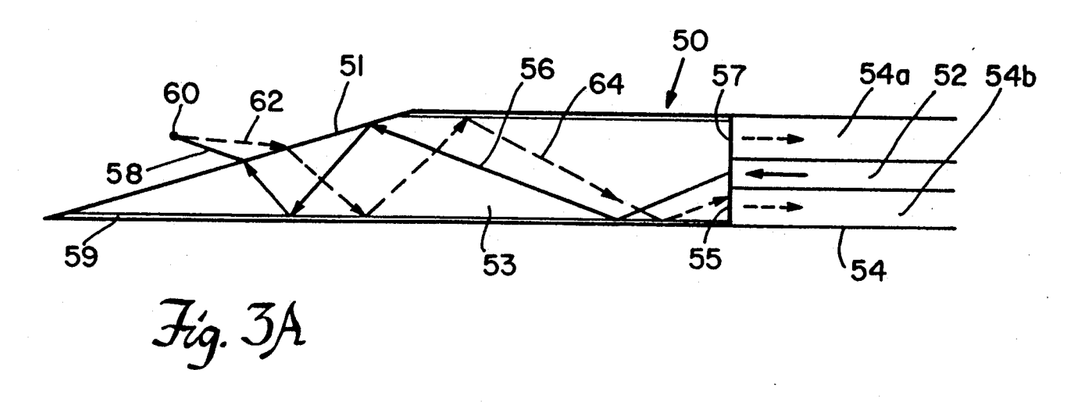
FIGS. 3A, 3B and 3C are schematic sectional and perspective views, respectively, of an "open needle" embodiment of the present invention.
Figure 3B:
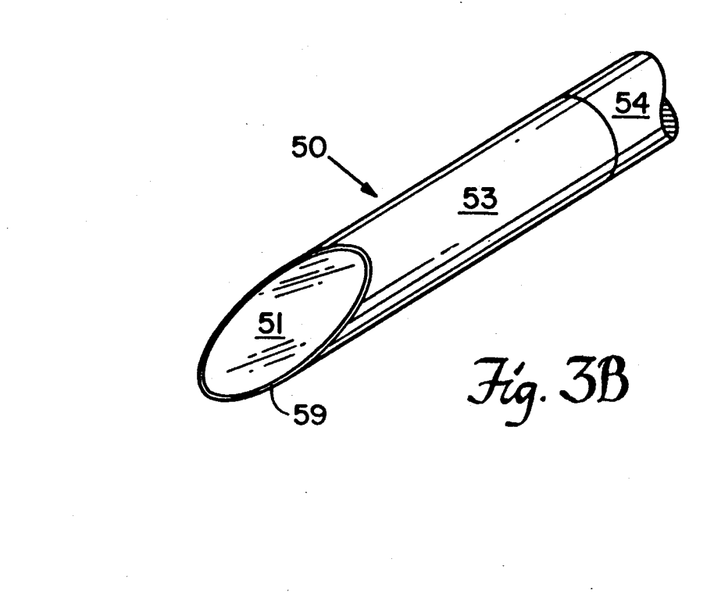
Figure 3C:
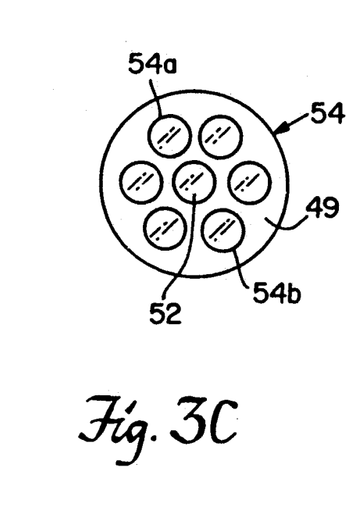

The "Open Needle" device 50 shown in FIGS. 3A, 3B and 3C closely resembles a hypodermic needle for which the angle of the tip is selected so as to slice into tissue and allow it to pass over the beveled surface 51.

In the case of this device, this action insures that the beveled optical sensing surface 51 is in clean, well defined contact with the tissue into which it is penetrating. The needle 50 has two basic components, an optically transparent tip 53 and an optical fiber bundle 54. The needle 53 has a proximal surface 55 that is optically coupled to the distal surface 57 of bundle 54.

The material used to form the optical needle 53, for example a synthetic sapphire, offers good mechanical strength, high index of refraction relative to the water in tissue, and excellent resistance to optical damage as well as easy sterilization and scratch resistance. A low index cladding 59 on the outside acts as an efficient reflector for most angles of incidence, while the metallizing on the outside surface of cladding 59 (not shown) captures the remaining rays. The bevel cut surface 51 which represents the active optical region has no cladding and is highly polished. The length and diameter of the needle are not critical to the extent that they are not mandated by specific applications. However, some gain in collection efficiency is obtained by expanding the diameter of the section of the needle adjacent to the coupling surface with the optical fibers so as to decrease the divergence of the return fluorescent light thereby obtaining a better match to the numerical aperture of the receiving fiber bundle.

Figure 4A:
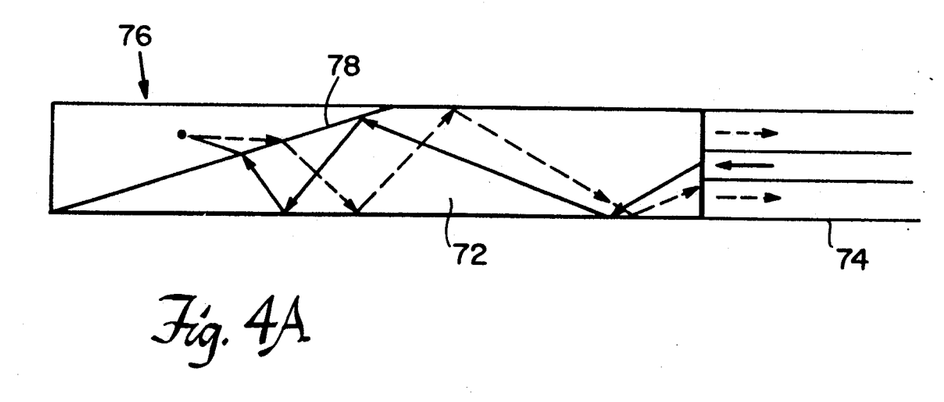
FIGS. 4A and 4B are schematic sectional and perspective views, respectively, of an "enclosed needle" embodiment of the present invention.
Figure 4B:
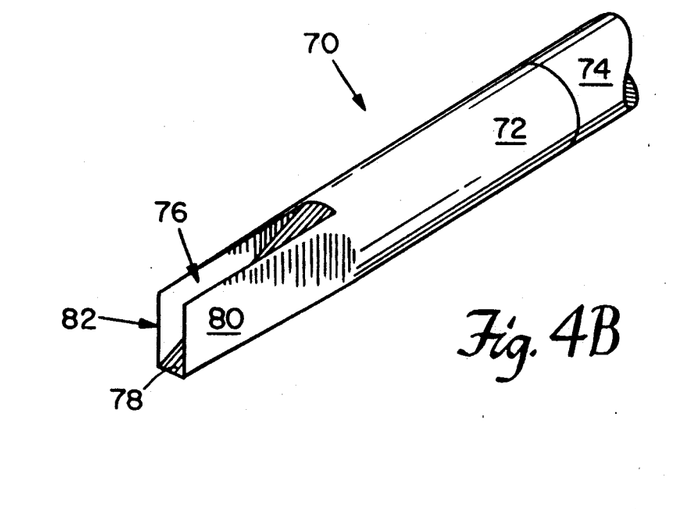

The device 70 shown in FIGS. 4A and 4B is closely related to that shown in FIG. 3, however, in this case the optical bevel cut surface 51 is replaced by a channel cut 76. Thus, the tissue that is translated across the bevel surface 78 is now surrounded on three sides by optically transmissive surfaces. Also, there are two bevel cuts 80,82 on the exterior surface of the sapphire rod which, however, is still reflecting on all exterior surfaces. The three leveled surfaces 78,80 and 82 define a U-shaped cutting edge at the distal tip of the needle 70. The Unshaped channel can have internal side walls that are orthogonal to surface 78 or the side walls and surface 78 can be formed as a single, rounded U-shape surface. One unique feature of this design is that the region 76 in which tissue fluorescence occurs is geometrically well defined by closely spaced surrounding walls. This greatly increases the light collection efficiency, and reduces or eliminates the dependence of the spectroscopic information produced upon uncontrolled variations in absorption and scattering effects.

Figures 5A, 5B:
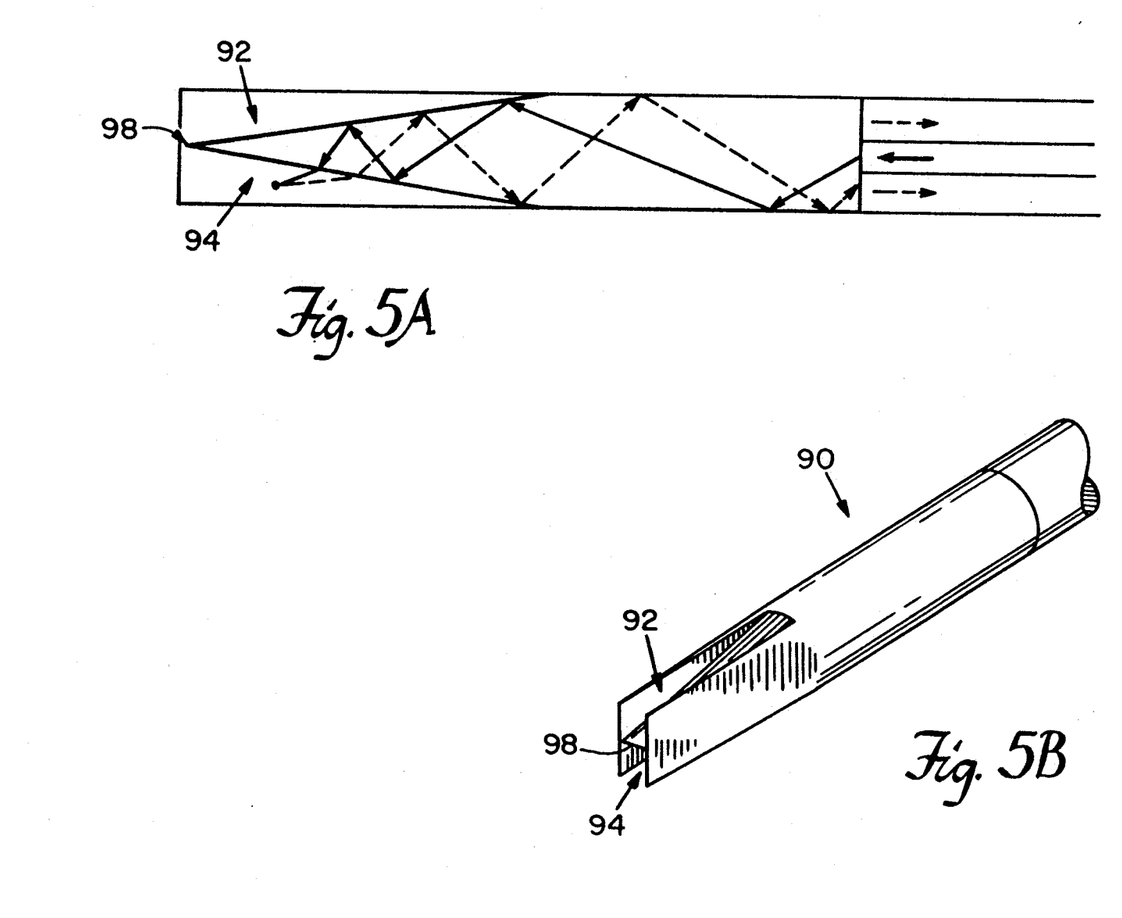
FIGS. 5A and 5B are schematic sectional and perspective views, respectively, of another preferred embodiment employing a double enclosed needle.

FIGS. 5A and 5B illustrate an alternative embodiment to that shown in FIG. 4B in which there are two enclosed bevel cuts providing for tissue to be cut along edge 98 and analyzed along two sides of the needle trajectory.

FIGS. 6-9 depict embodiments in which a needle or a bundle of optical fibers having a beveled surface are brought into contact with the tissue to be examined using a hypodermic needle as the cutting element. The use of a standard hypodermic needle provides for a stiff support for the optically conductive element which can either be permanently fixed to the needle, or can be inserted or removed therefrom after the proper positioning of the needle. This would permit the use of other endoscopic devices or the introduction of fluids or the removal of samples if appropriate.

Figures 6A, 6B:
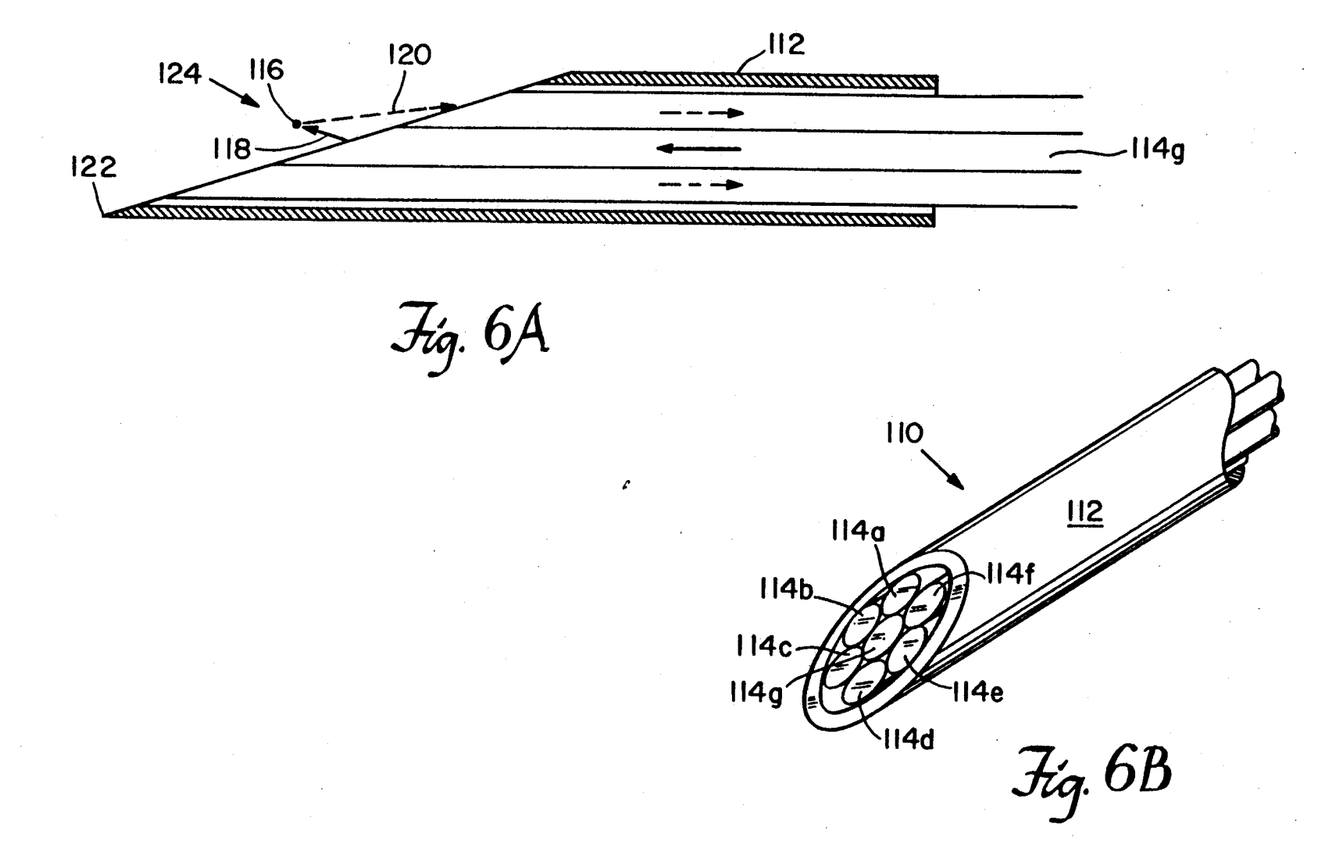
FIGS. 6A and 6B are schematic sectional and perspective views, respectively, of another preferred embodiment of the invention wherein an optical fiber bundle has been cleaved in a plane that coincides with the plane of the open end of a hypodermic needle in which the bundle has been inserted.

FIGS. 6A and 6B illustrate an embodiment of an optical needle 110 in which an optical fiber bundle having seven fibers 114a-114g are positioned within a hypodermic needle 112. The needle 110 has a cutting edge 122 along a portion of the peripheral tip of the hypodermic needle 112. The distal end of the fibers form a plane or distal surface 124 which is positioned to match the plane formed by the distal tip of the hypodermic needle. The fibers can be bonded together using a retaining device such as one of those described in U.S. Pat. No. 4,967,745, that was originally filed on Mar. 22, 1985, and which is incorporated herein by reference. The distal surface is formed by cleaving and polishing the multifiber plug as a unit. Light is projected along the central fiber 114g and is emitted 118 through surface 124, is absorbed by a portion of tissue 116 which then emits light 120. The light 120 is received by one or more of the fibers 114a-114f and transmitted to the proximal ends thereof for spectral and diagnostic processing.

Figure 7A:
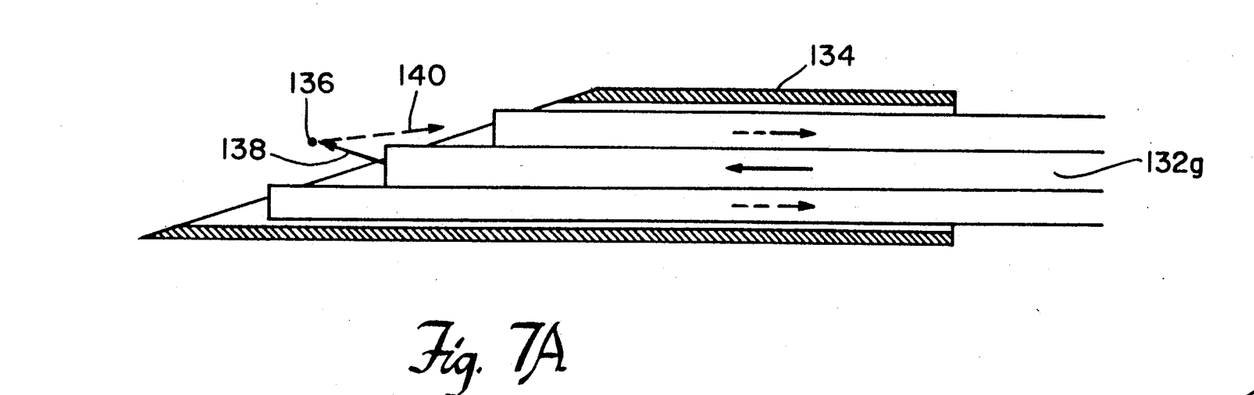
FIGS. 7A and 7B are schematic sectional and perspective views of a preferred embodiment in which the individual fibers are cleaved along planes perpendicular to the axis of the hypodermic needle in which the fibers are positioned.
Figure 7B:
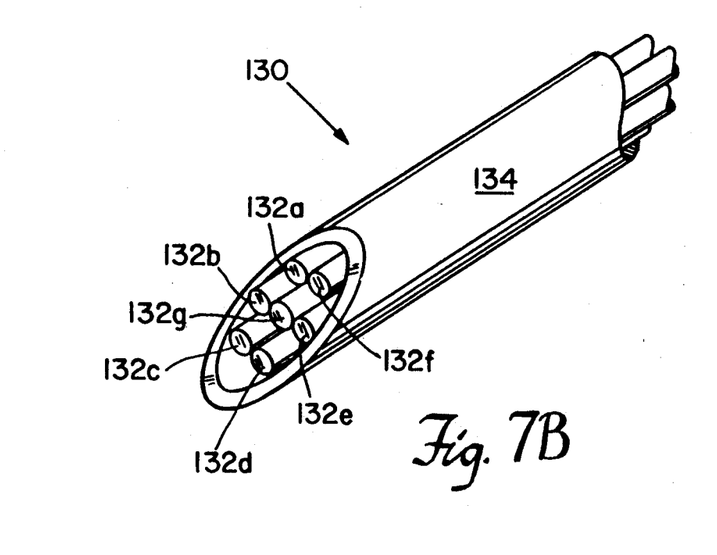

FIGS. 7A and 7B illustrate another preferred embodiment in which the distal surfaces of the fibers 132a-132g lie in planes perpendicular to the longitudinal axis of the fiber bundle within the hypodermic needle 134. The ends of the fibers 132a-132g are staggered along a plane that lies substantially in the plane formed by the distal tip of the needle 134. Although the embodiment shown utilizes seven fibers, with the central fiber 132g directing light 138 onto tissue portion 136 which then emits light 140 received by the collecting fibers 132a-132f, this embodiment can utilize a much larger number of fibers 132 such that the steps formed by the distal tips of the fibers are very small.

Figure 8A:
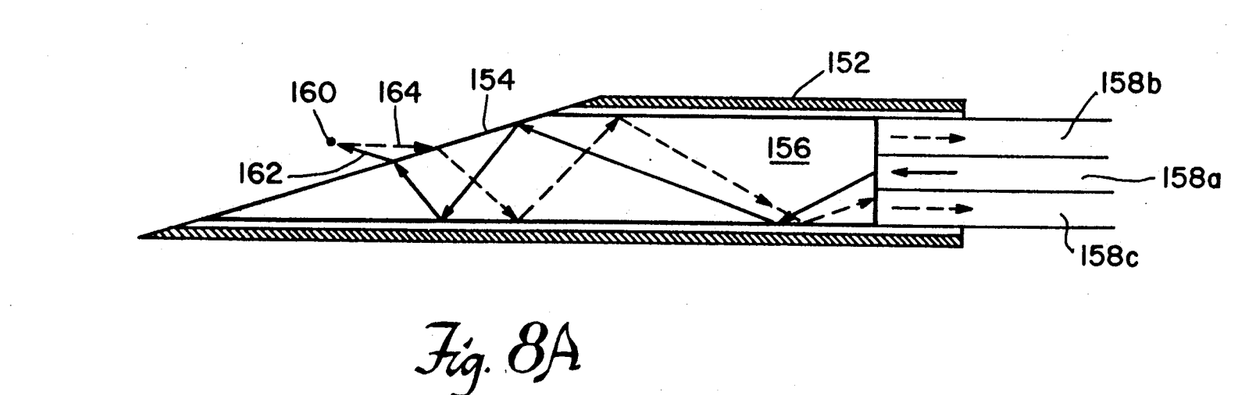
FIGS. 8A and 8B are schematic sectional and perspective views wherein the embodiment of FIG. 2 is used in conjunction with a hypodermic needle.
Figure 8B:
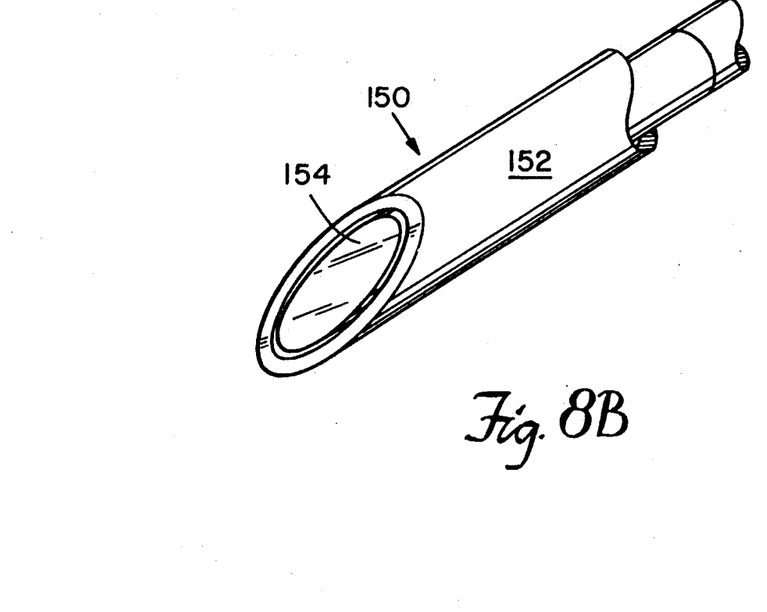

FIGS. 8A and 8B illustrate a preferred embodiment in which the device of an optical needle 150 is used in conjunction with a hypodermic needle 152. The distal surface 154 of the optical element 156 is formed so as to be coplanar with the distal tip of needle 152. The fibers 158a-158c deliver and receive light from element 156 which directs light 162 onto tissue portion 160 and collects the resulting emitted light 164.

Figures 9A, 9B:
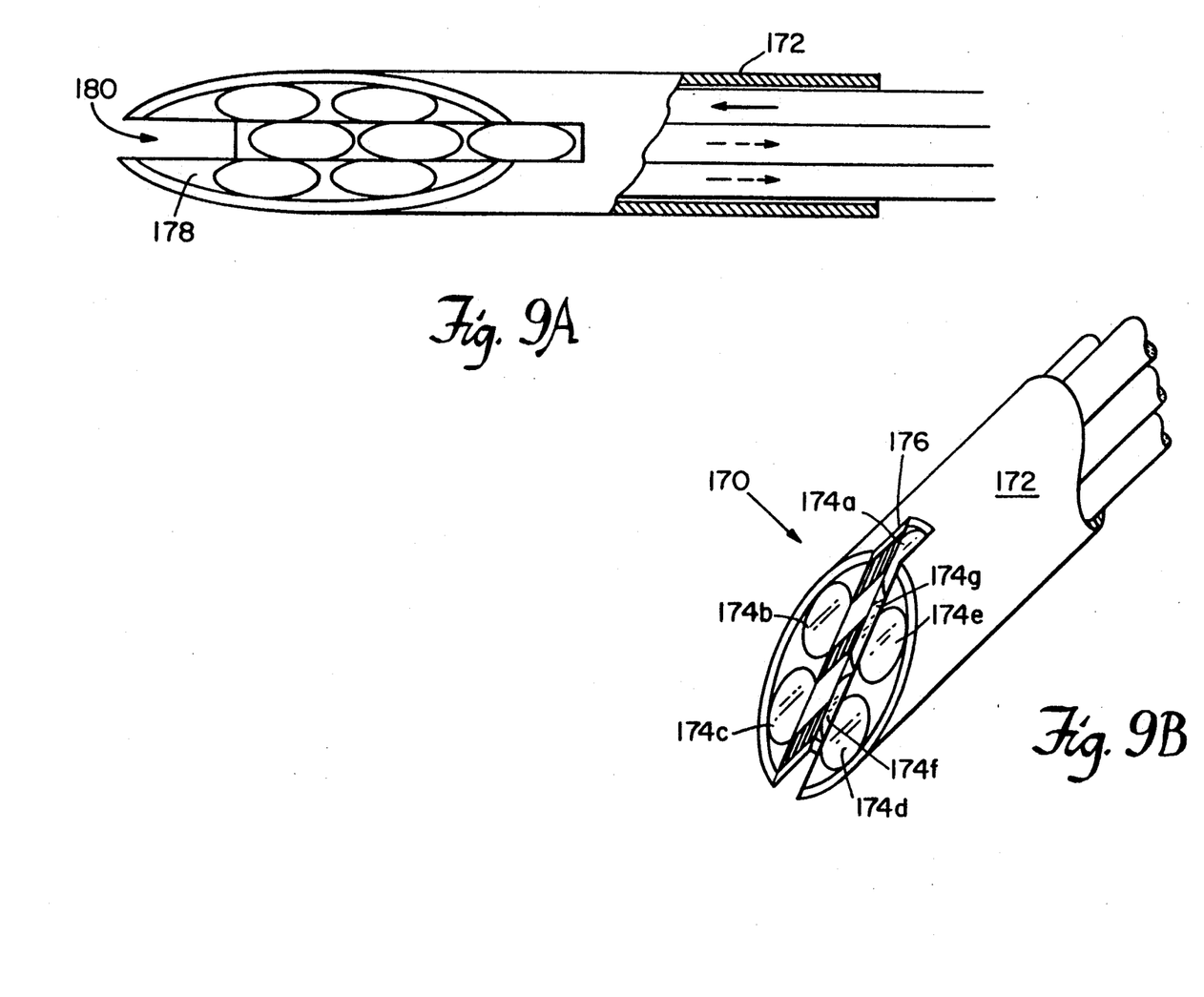
FIGS. 9A and 9B illustrate in partially sectioned and perspective views, respectively, another preferred embodiment in which the optical fibers form different surfaces in an enclosed needle configuration which is positioned within the tip of a hypodermic needle.

Another preferred embodiment is illustrated in FIGS. 9A-9B in which an optical needle 170 employs a bundle of fibers 174a-174g that are configured about a groove 180 extending through the tip of needle 170. The distal surface of the bonded fibers are cleaved and polished in the plane of the cutting angle of the hypodermic needle. The groove 180 surrounds the tissue slab cut by the needle edges. This device can function as a multifiber fluorescence device with all of the fibers connected in parallel.

Note that in one embodiment the leveled surfaces of fibers 174b, 174c, 174d and 174e, which are positioned on the outer plane of the needle, can be metallized to reflect light. The portions of these fibers facing the groove are not reflective such that if illuminating light is transmitted along fibers 174b and 174c, light can be collected with fibers 174a, 174f, and 174g located at the recessed surface of the groove, and also with fibers 174d and 174e having collecting regions directly opposite the illuminating fibers 174b and 174c within the groove 180. In this configuration, fibers 174a, 174f and 174g provide information regarding the scattering coefficient of the tissue. Fibers 174d and 174e provide information regarding the absorption coefficient of the tissue.

Diseased and normal tissue are known to possess distinguishing features in their fluorescence spectra. However, both absorption and scattering are known to alter the spectral characteristics of tissue so that it is desirable to determine their influence on measured fluorescence spectra and determine what diagnostically useful information is contained in absorption and scattering measurements independent of the fluorescence which is also occuring.

To determine the absorption of tissue which fluoresces at a specific wavelength upon illumination, two measurements of light emitted by the tissue must be performed. Light transmitted across tissue can be expressed generally as:

$$Y = Y_o e^{-\mu x} \qquad (1)$$

where Yo is the intensity of light entering a section of tissue of depth X, Y is the light emerging from the tissue, and u is the absorption coefficient of the tissue.

The first measurement determines the fluorescence yield of a section of tissue that is sufficiently thin. The yield can be expressed as:

$$Y_{thin} = AQ\,\mu_o x \qquad (2)$$

where Q is the quantum efficiency and A is a constant.

The second measurement determines the fluorescence yield of a sufficiently thick section of tissue where u is the absorption of the tissue.

$$Y_{thick} = AQ\mu_o \int e^{-\mu_o X} e^{-\mu x} dx = AQ\,(\mu/\mu_o + \mu) \qquad (3)$$

The ratio of these two measurements can be used $$Y_{thin}/Y_{thick} = [\mu_o + \mu]x = \mu_o x[1 + \mu/\mu_o] \qquad (4)$$

As shown in equation (4) to determine the light absorbed at the fluorescence wavelength. The scattering occurring in the tissue can also be determined using a similar calculation along with measurements of scattering in thin and thick samples.

The distal tip of the probe or needle can be formed to provide both an optical shield or needle tip as well as a retaining device for the optical fibers that deliver laser radiation to the distal surface of the device.

In the following method of manufacturing the catheter or needle probe an optically transparent high temperature polymer is extruded around one or more optical fibers to form at least the distal end of a catheter having a precisely defined geometry. The device can be used for both low or high energy laser light delivery and collection.

Figure 10:
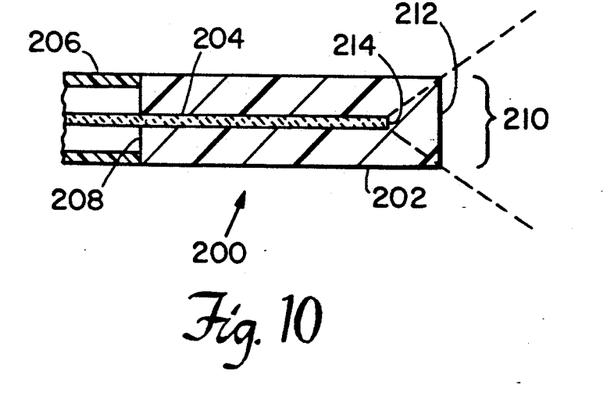
FIG. 10 is a sectional view of a preferred embodiment of an optical probe formed by the process of the present invention.

FIG. 10 illustrates a single fiber device 200 in which an optical fiber 204 is positioned within a solid polymeric material 202 that has been extruded over the fiber 204 to form a retaining optical shield. The shield 202 serves to precisely define the distance between the distal end 214 of the fiber 204 and the distal surface 212 of the shield such that light emanating from the fiber 204 will be transmitted through the entire area 210 of surface 212.

Note that the material 202 can be used to provide the entire catheter body used for insertion into the object being examined for any of the embodiments described herein. Alternatively, the material 202 can be coupled at the proximal surface to a catheter tube 206.

Figure 11:
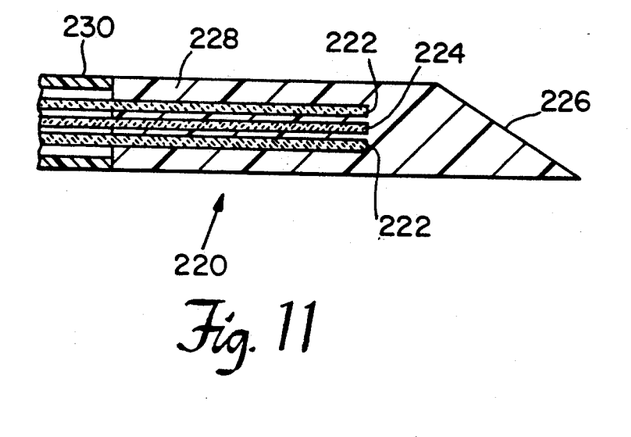
FIG. 11 is a sectional view of an optical needle formed by the process of the present invention.

FIG. 11 illustrates a multifiber needle device 220 formed by the present manufacturing process which could be used, for example, to form the embodiments shown in FIGS. 3-5. In the preferred embodiment of FIG. 11, a centrally configured illumination fiber 224 is spaced from, and surrounded by, a number of collection fibers 222. The precise configuration of the fibers 222, 224 relative to each other and the distal surface 226 is defined by the shield retaining material 228 which has been extruded over the fibers. The retaining shield 228 can be coupled to a catheter tube to complete the device.

Figure 12:
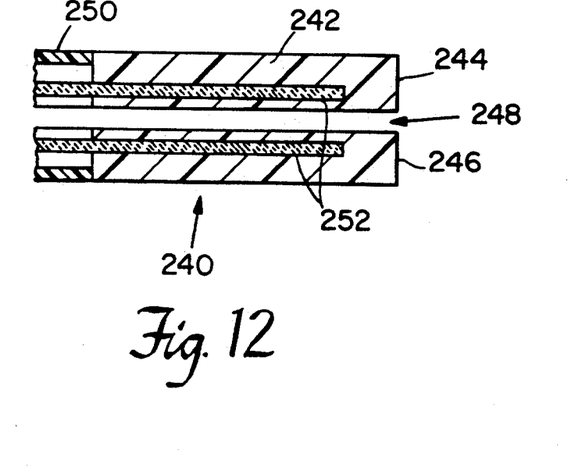
FIG. 12 is a sectional view of another preferred embodiment of an optical probe formed by the process of the present invention.

An alternative embodiment of a retaining shield 240 for a laser catheter is illustrated in FIG. 12 in which optical fibers 252 are secured within the extruded shield 242 in which the device has a centrally located lumen 248 that extends longitudinally through the core of the catheter. The lumen 248 provides for guidewire placement of the device, and further, provides fluid communication between the proximal and distal ends of the catheter.

As with earlier embodiments the material 242 can be coupled with a catheter tube 250, or can provide the entire catheter body.

Figure 13:
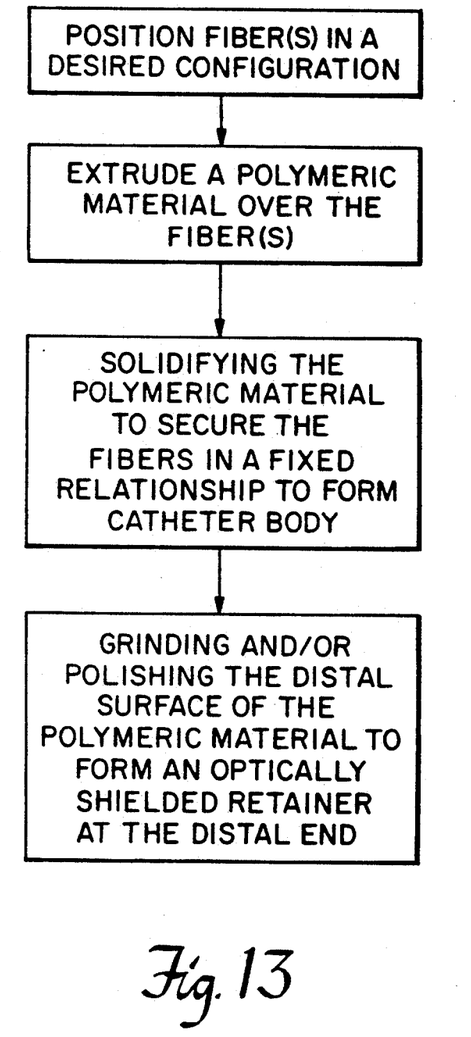
FIG. 13 is a process flow diagram that illustrates a manufacturing process.

The process for making a catheter is illustrated in the process flow diagram of FIG. 13. The fibers are held in position by a jig or other suitable positioning mechanism such that the portion of the fibers to be fixed in the catheter or needle tip are accurately positioned relative to each other in a predetermined configuration. A soft polymeric material is then extruded over the desired portion of the distal ends of the fibers. The extrusion is preferably in the shape of a cylinder whose longitudinal axis is along a central axis around which the fibers are symetrically arrayed. The material is soldified to secure the fibers in a fixed, spaced apart relationship and the distal surface is ground and polished to define an optical coupling surface that is a fixed distance from the ends of the optical fibers.

Due to the relatively low energy employed in diagnostic applications relative to those often encountered in some laser surgical procedures the present method provides a simple process for manufacturing diagnostic probe and needle components that couple light to tissue using material that are unsuitable for transmitting at higher energy levels.

For example, optically transparent polymers can transmit in the visible range between 400 and 500 nanometers at fluences of 100 millijoules/mm or less, which would be used for diagnostic applications at that wavelength.

Less transmissive but higher temperature polymers can be used at higher fluences employed for diagnostic applications in the infrared range, although low temperature polymers can also be employed.

Figure 14:
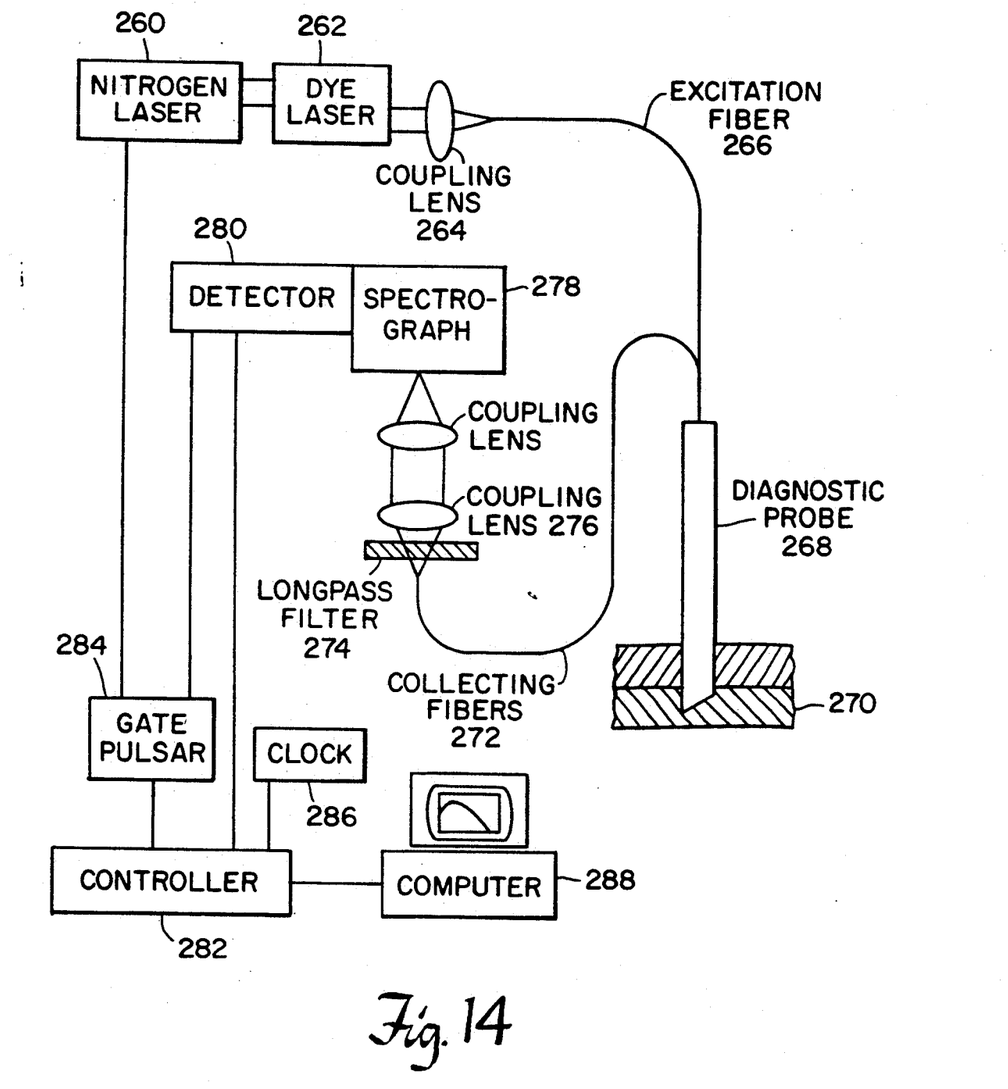
FIG. 14 is a schematic illustration of a preferred embodiment of the diagnostic system for the present invention.

Another preferred embodiment for a diagnostic system used for in vitro or in-vivo diagnosis of endogeneous tissue is illustrated in FIG. 14. In this embodiment a nitrogen laser 260 is used to pump a dye laser 262 in response to gate 284, controller 282, clock 286 and computer 288. Any solid state or other type of laser providing a suitable wavelength and energy level for diagnostic applications can be used. Radiation emitted by laser 262 is coupled to an excitation fiber 266 or fiber bundle with lens 264, and is transmitted through probe or needle device 268 to the tissue 270. The tissue than emits radiation in response to the excitation pulse or wave which is collected and transmitted through the collecting fiber or fibers 272 to coupling lenses 276. The emitted radiation is directed into spectral analyzer 278 and detector 280. The detector 280 generates an electrical signal that is correlated with selected spectral characteristics of the collected radiation. This signal can than be stored in the computers' memory, can be displayed or can be compared with a reference signal or spectrum that is also stored in the computers' memory. The laser employed for diagnostics or alternatively, a second laser, can be coupled to the probe or needle to deliver radiation for treatment or removal of tissue.

We claim:

1. An optical needle device for diagnosis of tissue comprising:

an optically transparent needle have a coupling surface, a tapered surface and a cutting edge for insertion into tissue to be diagnosed such that a converging optical channel is provided where light entering through the coupling surface is internally reflected by the tapered surface and is increasingly divergent as it progresses along the convergent channel until the angle of incidence of the light against the tapered surface exceeds a critical angle and is directed onto tissue contacting the tapered surface;

an optical fiber coupled to the coupling surface of the needle such that the light can be transmitted through the fiber into the needle and onto the contacted tissue to stimulate an emission of light by the tissue, the emitted light being transmitted through the needle and the optical fiber; and a light detector coupled to the optical fiber for receiving and detecting the light emission from the tissue.

2. The optical needle device of claim 1 wherein said needle further comprises a hypodermic needle having a distal opening and a lumen through which the optically transparent needle is positioned such that a plane formed by the distal surface lies in a plane formed by the distal opening.

3. The optical needle device of claim 1 further comprising a plurality of optical fibers that are optically coupled to the needle.

4. The optical needle device of claim 3 wherein the optical needle secures the fibers in a fixed spaced apart relationship.

5. The optical needle device of claim 1 wherein the detector comprises an analyzer that spectrally resolves the light emitted by the tissue.

6. The optical needle device of claim 5 wherein the analyzer comprises a spectrometer coupled to a distal end of the fiber to spectrally resolve the light emitted by the tissue.

7. The optical needle device of claim 1 wherein said optical needle comprises a groove projecting through a portion of the optically transparent needle such that a plurality of distal surfaces are formed defining the groove, each surface having a cutting edge for the incision of tissue.

8. The optical needle device of claim 7 wherein said groove comprises three distal surfaces such that tissue located within the channel is optically coupled to the three distal surfaces.

9. The optical needle device of claim 1 wherein said optical needle comprises a plurality of grooves projecting through a portion of the optically transparent needle.

10. The optical needle device of claim wherein the optically transparent needle comprises an optical fiber.

11. The optical needle device of claim wherein the optically transparent needle comprises an optical fiber bundle.

12. The optical needle device of claim 11 wherein a distal portion of the bundle is co red within a hypodermic needle.

13. The optical needle device of claim 11 wherein each fiber of the bundle has a distal surface which lies in a plane orthogonal to a longitudinal axis of the needle device.

14. The optical needle device of claim 11 wherein a distal end of each fiber of the bundle forms a single tapered distal surface.

15. The optical needle device of claim 1 further comprising a laser coupled to the optically transparent needle.

16. The optical needle device of claim 11 further comprising a channel having a plurality of distal surfaces wherein a selected number of fibers form each of the distal surfaces within the channel.

17. The optical needle device of claim 11 wherein one of said fibers couples a laser light source to the distal surface.

18. The optical needle device of claim 1 further comprising a source of laser radiation coupled to a distal end of the fiber to direct coherent radiation through the needle and into the tissue.

19. The optical needle device of claim 1 wherein the needle has a plurality of optical transmission surfaces through which light is directed onto tissue.

20. The optical needle device of claim 19 wherein the plurality of transmission surfaces comprises a first surface and a second surface such that light emitted through the first surface is directed through the tissue and onto the second surface.

21. An optical needle device for insertion and diagnose of tissue comprising an optically conductive needle having a cutting edge for the incision of tissue, a converging optical channel and a light transmitting distal surface that forms a groove extending along an exterior surface of the converging channel such that tissue cut by the edge is directed through the groove into optically conductive contact with the distal surface.

22. The optical needle device of claim 21 wherein said plurality of distal surfaces further comprises a first tapered surface, a second surface extending orthogonal to the first surface, and a third surface parallel to the second surface such that the first, second and third surfaces form a groove that surrounds tissue extending into the groove on three sides.

23. The optical needle device of claim 22 wherein the first, second and third surfaces extend to a cutting edge at a distal tip of the needle.

24. The optical needle device of claim 21 further comprising a bundle of optical fibers coupled to a proximal end of the optical channel.

25. The optical needle device of claim 21 further comprising a plurality of converging channels, each channel extending along an optical fiber having a beveled distal surface.

26. The optical needle device of claim 25 further comprising a hypodermic needle through which the fibers extend.

27. The optical needle device of claim 21 further comprising a second groove extending along the exterior surface of the converging channel.

28. The optical needle device of claim 21 further comprising a laser coupled to the converging optical channel.

29. The optical needle devices of claim 21 further comprising a plurality of grooves extending along the convergent channel.

30. A method of diagnosing tissue comprising:
inserting an optical needle with a cutting edge into tissue to be diagnosed;
positioning a distal surface of an optically transparent element of the needle in contact with a portion of the tissue;
coupling a light source to the optically transparent element to conduct light along an optically convergent path such that the light is internally reflected becoming increasingly divergent until the angle of incidence of the light against the channel exceeds a critical angle and is transmitted through the distal surface and illuminates the portion of tissue;
collecting light emitted by the tissue in response to the illuminating light with the optically transparent element; and
analyzing the collected light to diagnose a condition of the tissue.

31. The method of claim 30 further comprising coupling a laser light source to the element to deliver radiation to the tissue to treat the tissue.

32. The method of claim 30 further comprising coupling the light source to the optically transparent element with an optic fiber.

33. The method of claim 3 further comprising coupling the optically transparent element to an analyzer with an optical fiber bundle.

34. The method of claim 3 further comprising inserting the needle into tissue such that the tissue is directed into a groove extending through the distal surface.

35. The method of claim 30 wherein the analyzing step comprises comparing a characteristic of the collected light with a reference.

36. The method of claim 30 rein the analyzing step further comprises coupling the collected light to a spectrometer.

37. The method of claim 3 wherein said optically transparent element comprises an optical fiber.

38. The method of claim 30 further comprising positioning the optically transparent element into a hypodermic needle such that the distal surface lies in a plane of a cutting angle on the needle.

39. The method of claim 3 wherein the optically transparent element comprises an optical fiber bundle.

40. The method of claim 38 wherein the optically transparent element comprises a plurality of grooves extending through the distal surface to receive the portion of tissue to be diagnosed.

41. A laser optical needle system for diagnosis of tissue comprising:
a laser source provide radiation for delivery to the tissue to be diagnosed;
an optically transparent needle having a coupling surface, a tapered surface and a cutting edge for insertion into tissue to be diagnosed such that a converging optical channel is provided where light entering through the coupling surface is internally reflected by the tapered surface and is increasingly divergent as it progresses along the convergent channel until the angle of incidence of the light against the tapered surface exceeds a critical angle and is directed onto tissue contacting the tapered surface;
a plurality of optical fibers coupled at a distal end of each fiber to the coupling surface of the needle and at a proximal end of at least one of the fibers to the laser source such that laser radiation transmitted through the fibers into the needle and onto the contacted tissue to stimulate an emission of light by the tissue, the emitted light being transmitted through the needle and the optical fibers; and a spectral analyzer coupled to the proximal end of at least one of the optical fibers to receive the emitted light.

42. The optical needle device of claim 41 wherein said needle further comprises a hypodermic needle having a distal opening and a lumen through which the optically transparent needle is positioned such that a plane formed by the distal surface lies in a plane formed by the distal opening.

43. The optical needle device of claim 42 further comprising a detector to detect the spectrally resolved light.

44. The optical needle device of claim 41 wherein said optical needle comprises a groove projecting through a portion of the optically transparent needle such that a plurality of distal surfaces are formed defining the groove, each surface having a cutting edge for the incision of tissue.

45. The optical needle device of claim 44 wherein said groove comprises three distal surfaces such that tissue located within the channel is optically coupled to the three distal surfaces.

46. The optical needle device of claim 41 wherein said optical needle comprises a plurality of grooves projecting through a portion of the optically transparent needle.

47. The optical needle device of claim 41 wherein the optically transparent needle comprises an optical fiber bundle.

48. The optical needle device of claim 47 wherein a distal portion of the bundle is configured within a hypodermic needle.

49. A method of manufacturing an optical probe comprising:
   securing a plurality of optical fibers in selected configuration relative to each other;
   extruding a polymeric material about the fibers;
   hardening the material to secure the fibers relative to each other to form at least a portion of the probe body; and
   polishing a distal end of the material to form an optical shield over the distal ends of the fibers to optically couple the distal ends of the fibers with the distal surface of the shield.

50. The method of claim 49 wherein the distal surface forms an optical needle having an edge for the incision of tissue.

* * * * *

UNITED STATES PATENT AND TRADEMARK OFFICE
CERTIFICATE OF CORRECTION

PATENT NO. : 5,280,788
DATED : January 25, 1994
INVENTOR(S) : G. Sargent Janes and Gary B. Hayes It is certified that error appears in the above-indentified patent and that said Letters Patent is hereby corrected as shown below:

Column 1, lines 10-13, insert:

---Government Support

This invention was made with government support under Grant No. NIH-2-P41-RR02594 by National Insitutes of Health. The government has certain rights in the invention.---

Signed and Sealed this

Twenty-ninth Day of October 1996

Attest:

BRUCE LEHMAN

*Attesting Officer*     *Commissioner of Patents and Trademarks*